United States Patent [19]

Bonner et al.

[11] 4,155,714
[45] May 22, 1979

[54] PROCESS AND APPARATUS FOR CONVERSION OF ATZ TO PTH AMINO ACID DERIVATIVES OF PROTEINS

[76] Inventors: Alex G. Bonner, 23 Fairway Dr., West, Newton, Mass. 02165; Marcus J. Horn, 1106 Boylston St., Newton, Mass. 02164

[21] Appl. No.: 892,400

[22] Filed: Mar. 31, 1978

[51] Int. Cl.² .......................................... C07C 103/52
[52] U.S. Cl. .............................. 23/230 R; 23/230 A; 260/112.5 R; 422/109
[58] Field of Search ............ 23/253 A, 253 R, 230 A, 23/230 B, 230 R, 252 R; 260/112.5 R

[56] References Cited

U.S. PATENT DOCUMENTS

| | | | |
|---|---|---|---|
| 3,531,258 | 9/1970 | Merrifield et al. | 23/252 R |
| 3,557,077 | 1/1971 | Brunfeldt et al. | 23/253 A |
| 3,647,390 | 3/1972 | Kubodera et al. | 23/253 A |
| 3,725,010 | 4/1973 | Penhasi | 23/253 R |
| 3,951,741 | 4/1976 | Pfaender | 23/253 A |
| 4,065,412 | 12/1977 | Dreyer | 23/253 R |

Primary Examiner—R. E. Serwin

[57] ABSTRACT

A process and apparatus for the conversion of anilino-thiazolino amino acid derivatives of peptides and proteins for use with conventional sequencers in the overall Edman degradation process. The apparatus comprises a modular unit separate from the sequencer having an independently programmable control and flow actuating and directing means including a source of pressurized nitrogen, a conversion reagent container, a wash solvent container, a reaction vessel, and a plurality of interconnecting tubes and valves controlled so as to regulate the amounts and durations of all fluids entering and leaving said reaction vessel under gas pressure.

The process comprises performing the steps of conversion, sample recovery, drying and washing at temperatures below but near to the respective boiling points of both the reagent and the solvent, and under reflux tower conditions. A specific embodiment employs anhydrous methanolic hydrogen chloride for the reagent and dichloroethane methanol (7:3) for the solvent, and both the conversion and the washing are done at 65° C., in a reaction vessel comprising a lower, heated portion, and an upper, cooled portion where the reflux action takes place both during the conversion and washing steps.

12 Claims, 2 Drawing Figures

PROCESS AND APPARATUS FOR CONVERSION OF ATZ TO PTH AMINO ACID DERIVATIVES OF PROTEINS

BACKGROUND OF THE INVENTION

1. Field of the present invention

The field of the present invention is the automatic conversion of the anilinothiazolino derivatives (ATZ) to the phenylthiohydantoin derivatives (PTH) of peptides and proteins in the well-known Edman degradation process.

2. Description of Prior Art

The principles of the solid phase Edman degradation technique for high sensitivity analysis of peptides and proteins are well-known. Briefly, the process can be described as follows. First, the protein or peptide is covalently bonded to an inert support, such as a polystyrene or glass support. While in a reaction column or vessel, this peptide or protein undergoes a coupling step using phenyl isothiocyanate (PITC) which may be in the radioactive form when labelling is desired. A buffer solution is pumped simultaneously with the PITC, and preferably for a period of time thereafter to clean the lines. After the coupling step, the phenylthiocarbamyl peptide or protein is alternately washed with methanol and with dichloroethane. The sample then undergoes a cleavage step by being treated with anhydrous trifluoroacetic acid. After the cleavage step, the protein or peptide derivatives in the reaction column are preferably washed with methanol. The resulting product after this cleavage step is an anilinothiazolinone (ATZ) amino acid derivative, which is usually unstable and normally requires a conversion step to a phenylthiohydantoin (PTH) amino acid derivative. These PTH derivatives are then identified by conventional means of chromatography.

The first two of these steps (viz. coupling and cleavage) have been automated, and incorporated into automatic "sequencers" (see U.S. Ser. No. 803,689 entitled "Microsequencing System for the Sequencing of Peptides and Proteins" by A. Bonner and M. Horn and references cited therein). These sequencers have gained general acceptance by offering many advantages over manual methods, among these being the time- and labor- saving aspects of automation, and the improved per-cycle yields, allowing a larger number of repetitive degradative steps to be performed on a peptide or protein sample.

The automation of the conversion step, however, has not kept pace with the automation of the other two steps. Several prototype conversion devices have been constructed for particular applications. One such known device is described by B. Wittmann-Liebold et al., in Analytical Biochemistry, Vol. 75, pp. 621–633 (1976), and in the German Offenlegungsschrift No. 2,208,088.

Several factors influenced the design considerations of the prior art. Thus, since the automated main sequencers of the prior art were already provided with programmers, controls, and supplies for nitrogen and vacuum, and since these relatively expensive components were also needed for automatic conversion, the trend of the industry was uniformly toward incorporation of the conversion apparatus into the main sequencer in order to avoid duplication. Incorporation of the conversion devices in the main sequencers, however, brought about various disadvantages. For example, major modifications were required in the electronics of the main sequencer, and since there are many different types of main sequencers, the prior art modifications for the conversion devices were therefore useful only in the particular sequencer into which they were incorporated. In addition, as a result of total incorporation into the main sequencer, the prior art conversion devices were synchronously tied to the main sequencer in such a way that neither the main sequencer nor the conversion component had independent versatility of operation or control. An additional drawback of the integrated systems of the prior art was that the operation of the conversion device also required simultaneous operation of the main sequencer, and as a result, at the end of the last conversion step, there would always remain in the reaction cell of the main sequencer one cycle's worth of unconverted sample. This resulted in loss of material and inefficient use of sequencing reagents, a matter of particular significance when the quantities of sample available are extremely small, and when the reagents are extremely costly.

SUMMARY OF THE INVENTION

The present invention comprehends both a process and an apparatus for use as an independent unit along with a main sequencer in the overall Edman degradation process. The purpose is to provide automatic conversion of anilinothiazolinone (ATZ) amino acid derivatives to the more stable phenylthiohydantion (PTH) amino acid derivatives of protein and peptides. The need for the conversion step and its automation is dicated by several considerations:

(1) the instability of the thiazolinone (ATZ), (2) the instability of certain amino acid residues while in the ATZ form, (3) the need for step-to-step reproducibility for quantitation, (4) efficiency of sample utilization, (5) minimization of solvent and reagent requirements, (6) minimization of wash-cycle time, and (7) the desireability of providing a versatile conversion unit which can be readily interfaced with other inline systems to provide for a totally automated chromatographic identification of the amino acid phenyl thiohydantoin.

The auto-converter of the present invention is an independent, modular, add-on unit, which interfaces with existing solid phase and liquid phase automatic main sequencers. (Herein the term main sequencer is used to define the sequencer controlled by the main programmer, which performs the preceding steps in which the proteins and peptide are degraded to the ATZ derivatives). The auto-converter of the present invention is completely self-contained, and contains its own programmer. Briefly, the auto-converter comprises a control unit and a valves unit. The control unit is programmable, and has the capability of both manual and automatic operation.

The valves unit comprises a system of valves interconnected with tubing, and employs nitrogen gas under pressure for the delivery of reagents and solvents. The valves control the flow of all the various fluids involved in the conversion process. The valves unit also comprises a reaction vessel or cell in which the sample ATZ derivatives are converted to PTH derivatives. The lower part of this reaction cell is preferably partially surrounded by a thermostatically controlled aluminum block heater and the upper part is allowed to cool so as to provide reflux tower conditions. The valves unit employs a reagent bottle containing the reagent for effecting the PTH-ATZ conversion, and a bottle for the solvent used to wash the PTH derivatives from the reaction cell, and to convey the sample to the main sequencer fraction collector after conversion.

The process of the present invention is directed toward increasing the efficiency of the conversion step, by the reduction of reagent and solvent utilization; by the reduction of time required for the conversion, drying and washing steps; by the standardization of sample amounts, and the coordination of the sample amount with the reaction, drying, washing and transfer cycle times; and the reduction or prevention of loss of sample.

These objects are met by a combination of various steps. First, automated cycle programming is provided together with adjustable time control whereby sample amounts and the cycle times of reaction, drying, and washing are accurately controlled. Efficient washing as well as efficient sample utilization are accomplished by arranging the reaction vessel with a heated lower portion and a relatively cool upper portion and maintaining the temperature of the lower portion close enough to the boiling points of the liquid (reagent or solvent) so that reflux conditions are established so as to bath the upper sides of the reaction vessel and constantly return any portions of the sample which may find their way up the sides of the vessel, to the reaction area. This permits the operator to increase the temperature to a level close to the boiling point of the reagent thereby accelerating the reaction rate without fear of loss of sample due to boiling or splattering of the sample up the walls of the vessel. It also permits him to bubble nitrogen through the sample for mixing at a higher rate likewise without fear of loss of sample on the walls of the vessel. Finally it greatly improves the efficiency of washing thereby reducing the number of washing cycles and the amount of solvent required to completely wash the reaction vessel. In the preferred practice the process is carried out with the lower part of the reaction vessel at 65° C., using methanolic hydrogen chloride for the reagent and dichloroethane/methanol (7:3) for the solvent. In this way the conversion is accomplished under milder conditions than the aqueous methods of the prior art. The greater volatility of the reagent permits faster drying. Also, the conversion reaction employing methanolic/HCL results in the production of methyl esters of glutamic and aspartic acid which do not require special modification prior to gas chromatography. In addition, the methanolic/HCL is simply and accurately formulated. Moreover, these ingredients provide optimum conditions for drying, reflux action, conversion, and washing without requiring any change in temperature of the reaction vessel.

Accordingly, an object of the present invention is to provide a conversion unit which is completely independent of the main sequencer, and at the same time compatible with any main sequencer. Its independence allows complete flexibility of not only the converter but also of the main sequencer. This independent programmability of the auto-converter thus advantageously permits the experimenting scientist to readily modify the program so as to perform different conversion methods. For example, the auto-converter can be programmed to perform the standard 20% acqueous trifluoroacetic acid (TFA) conversion; or it can be easily modified to perform the Appella-Inman PTC-amide conversion which uses methyl amine gas or methyl amine in isopropanol as the conversion reagent. However, it is uniquely suited for conversion using methanolic/HCL reagent and dichloroethane/methanol solvent at 65° and under reflux conditions.

A further object to the present invention is to provide a small, compact automatic conversion device.

An additional object of the present invention is to provide an inexpensive automatic conversion device, which can be easily interfaced with all existing main sequencers.

Still a further object of the present invention is to provide a conversion device capable of both automatic and manual operation.

Finally, an object of the present invention is to yield superior results over existing automatic converters, by improving the yield of the stable converted PTH derivatives.

DETAILED DESCRIPTION OF THE PREFERRED EMBODIMENT

Figure 1:
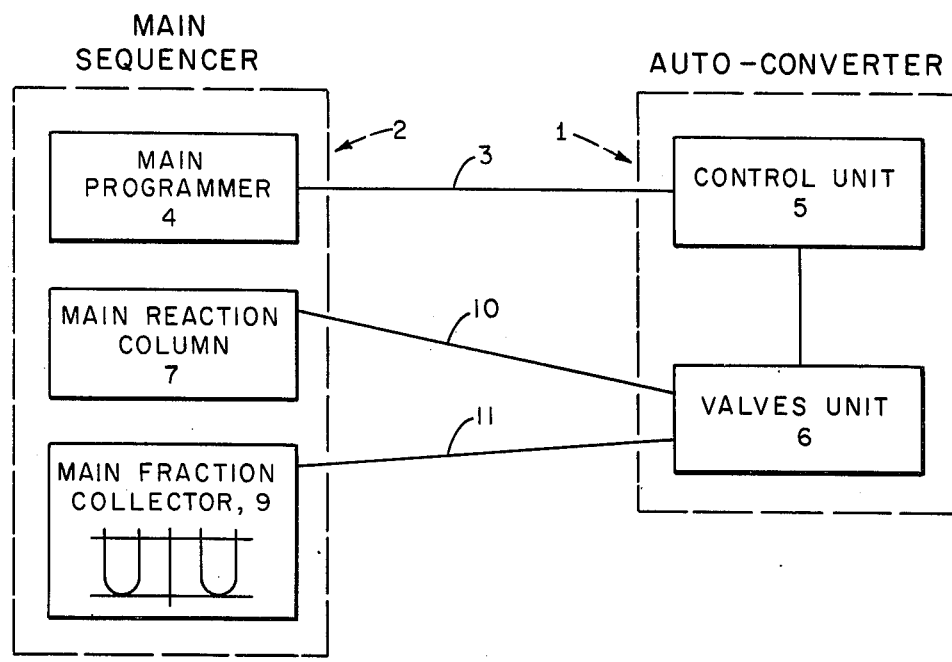
FIG. 1 is a schematic view showing the connections between the automatic conversion device of the present invention and a main sequencer.

With respect to FIG. 1, therein is shown in schematic form how the modular automatic conversion device, designated generally as 1, is interfaced with an existing main sequencer, designated generally as 2. As for the electronics, a simple wire connection 3 is established between the main sequencer 2 and the auto-converter 1, through which the auto-converter start signal is sent by the main programmer 4 to the control unit 5 of the auto-converter. This start signal can be easily programmed into the main programmer 4, such as by punching a hole in the main programmer tape. After the start signal is received from the main programmer 4, the auto-converter 1 will run completely independently of the main programmer. Although not shown in FIG. 1, the auto-converter 1 is connected by an AC power source, and can therefore be operated independently of the main sequencer. Also, the start signal can be fed into the auto-converter control unit 5 manually or by means other than by a signal from the main programmer 4.

Upon receipt of the start signal, the program of the control unit 5 is initiated. The control unit will have been previously programmed by well known means to dictate which valves should be opened or closed, at what times, and for what length of time. In other words, the control unit 5 controls the position of all the valves in the valves unit 6 of the auto-converter at every point in time.

The first step of the auto-converter program is to bring the peptide or protein sample from the main reaction column (or cup) 7 of the main sequencer 2 into the valves unit 6 of the auto-converter. It should be noted that, as shown in FIG. 1, two simple and superficial modifications must be made to the main sequencer 2. First, a tube 10 must be connected between the main reaction column 7 and the auto-converter reaction cell 8; second, a tube 11 must be connected between the auto-converter reaction cell 8 and the main fraction collector 9, to which the finally converted sample is ultimately delivered.

Figure 2:
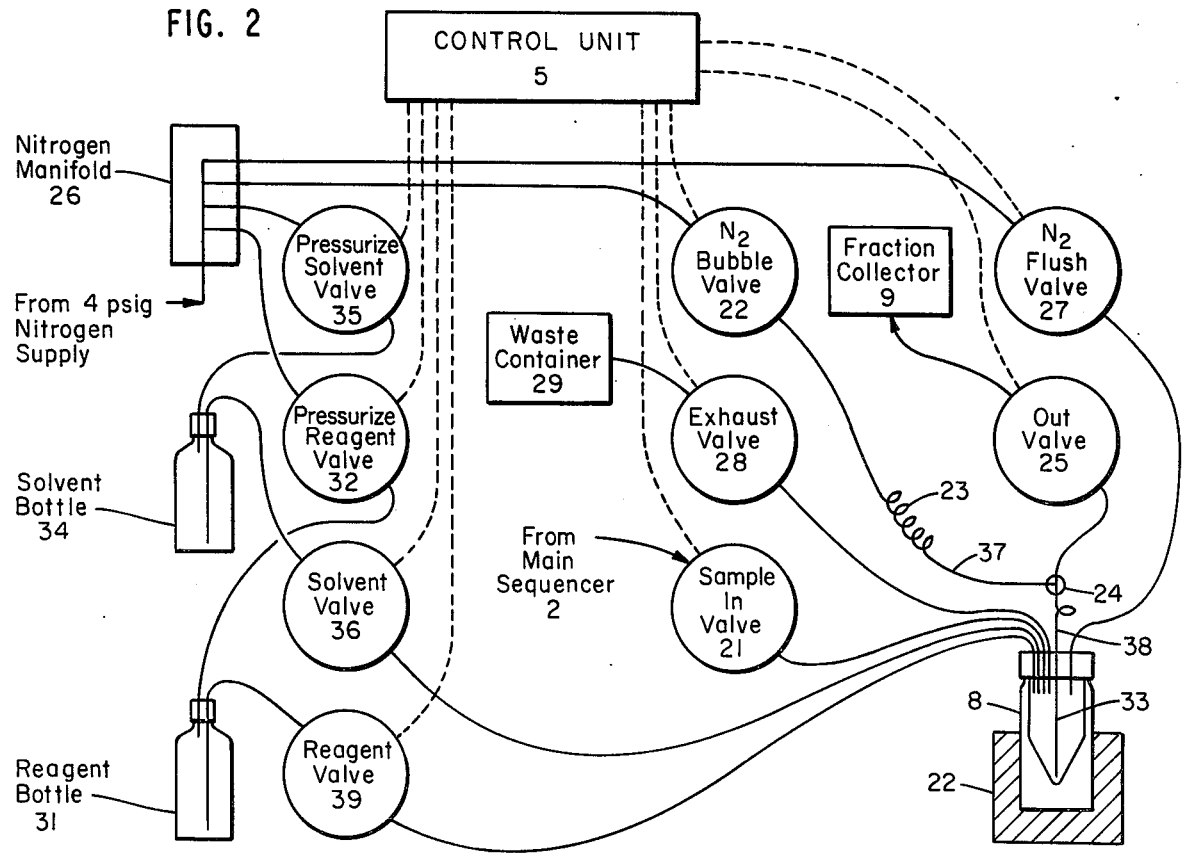
FIG. 2 is an overall schematic view of the automatic conversion device of the present invention.

Returning again to the connecting tube 10 between the main reaction column 7 and the auto-converter reaction cell 8, this tube is shown more specifically in FIG. 2, viz. the sample (e.g., 2.5 ml) is delivered from the main reaction column 7 through the "sample in" valve 21 through Teflon tubing into a reaction vessel or cell 8 of the auto-converter. The reaction cell 8 may conveniently be a 5 ml REACTI-VIAL with fitted Teflon cap and Teflon washer to provide a leak-tight seal. The lower half of the cell is surrounded by an aluminum block 22 the temperature of which is thermostatically controlled. The upper half is open to ambient, cooling air in order to establish reflux conditions. A cooling jacket (not shown) may be provided if additional cooling is desired. After the sample is introduced into the reaction cell 8, the control unit closes the "sample in" valve 21. The step of introducing the sample into the reaction cell 8 may take as long as 15 minutes during which time dry nitrogen is being blown over the sample and bubbled through it. After the sample is fully introduced, the drying is continued until completion. Drying is carried out at approximately 65° C. The nitrogen gas for the bubbling is delivered from a nitrogen manifold 26 through the "$N_2$ bubble" valve 22, through a restrictor tube 23 (whose function will be more fully described below), through a T-coupling 24, and into the bottom of the reaction cell 8. An "out" valve 25 for removing the sample after conversion is in the closed position during nitrogen gas bubbling. The nitrogen gas which is blown over the surface of the sample in the reaction cell 8, is delivered from the nitrogen manifold 26 through the "$N_2$ flush" valve 27 through the cap of cell 8. During both the bubbling and flush drying steps, which occur simultaneously and often last 15–20 minutes, an "exhaust valve" 28 will be in the open position, thereby allowing the vapor laden nitrogen to exhaust to a waste container 29. As noted previously, the positions of all the valves at all times are governed by control unit 5 according to its program. Although nitrogen gas is used, other gases (preferably non-oxygen containing) may also be satisfactorily used so long as they are inert relative to the sample or mixture in the reaction cell 8.

After the sample drying step has completed, the control repositions the valves and the reagent addition step is initiated. During this step, approximately $\frac{3}{4}$ ml anhydrous 1–2N methanolic hydrogen chloride is added to the dried sample in the reaction cell 8. This reagent is prepared by making a 1–2N solution (under ice cooling) of acetyl chloride in methanol. It should be noted, however, that although the specific ingredients used and the related process steps described herein offer special advantages, the apparatus of the present invention permits the use of other conversion reagents. For example, the conversion agent can be aqueous 20% trifluoroacetic acid; or methyl amine gas or methyl amine in isopropanol, as in the Appella-Inman PTC-amide conversion; or the conversion reagent could be aqueous hydrochloric acid in MeOH as in the Tarr procedure (see, e.g., Tarr, G.E. (1975) Analytical Biochemistry Vol. 63, p. 361). It can be readily seen therefore that the present invention can be easily applied to many different conversion procedures, by simply selecting the desired reagent and adjusting the control unit 5 for the desired duration of reagent addition step. In addition various advantages of the process steps relating to maintaining reflux conditions can be obtained using other ingredients simply by regulating the temperature to correspond to the reagents and solvents used.

Now the reagent, anhydrous 1–2N HCl in MeOH, is added to the reaction cell 8, will now be described. With the reagent in reagent bottle 31, the control unit 5 opens pressurized reagent valve 32. This results in the flow of nitrogen gas from the nitrogen manifold 26 under 4.5 psig. The nitrogen comes from an external source not shown which supplies the required pressure. The nitrogen gas thus brings the pressure in the reagent bottle 31 up to 4.5 psig. The control unit 5 then opens "reagent valve" 39 and the reagent under the nitrogen gas pressure in the reagent bottle 31 flows through the "reagent valve" 29 into the reaction cell 8. After the programmed time for the reagent addition step has elapsed, the control unit 5 closes the reagent valve 39.

During the above-mentioned reagent addition step, the control unit 5 also keeps the "$N_2$ bubble" valve 22 and "exhaust valve" 28 open, to permit gentle agitation and mixing of the sample with the reagent. As shown in FIG. 2, there is a restrictor tube 23 in the line between the "$N_2$ bubble" valve 22 and the reaction cell. The function of this restrictor tube 23 is to reduce the effective pressure from 4.5 psig, and to bring about gentle mixing and agitation. In addition, a back-up loop 38 compensates for capillary action and pressure differential flows, and thereby prevents any unconverted part of the sample from being drawn up into the $N_2$ bubble tube 23. The bubbling step is preferably continued for a predetermined time after completion of the delivery of the reagent in order thoroughly to mix the sample and the reagent. Thereafter, the "$N_2$ bubble" valve 22 is closed and the sample in the cell 8 is allowed to stand for 6–8 minutes to complete the conversion reaction. During this standing period, the sample is kept at the reaction temperature of 65° C. Due to its heated lower part and cooled upper part, the cell 8 serves as a reflux tower, thereby assuring a continuous flow of the reagent and sample traces back into the lower part of the cell 8. The refluxing occurs in the following manner. Since the heater heats only the bottom half of the reaction cell 8, as the liquid sample in the cell evaporates it condenses on the side walls of the upper part of the cell and also somewhat on the tubes which extend downwardly inside the cell. In the preferred embodiment, the heater 22 is maintained at 65° C., which is slightly above the boiling point of MeOH. The condensation drips back into the bottom heated portion of the cell, and as it does so, it washes the walls and carries back all residue of the sample which may have found its way up the walls due to liquid boiling or nitrogen bubbling. As a result there is an extremely thorough mixing of the PTH sample with the conversion reagent in the cell 8.

After the mixture has been allowed to stand during the conversion step, another drying step is initiated by the control unit 5. This drying step is performed in the same manner as the earlier discussed drying step. In brief, the "$N_2$ bubble" valve 22, "$N_2$ flush" valve 27, and "exhaust valve" 28 are placed in the open position by the control unit for a pre-programmed period of time. At the end of this drying step, the "$N_2$ flush" valve and the $N_2$ bubble valve 22 are again placed in the closed position by the control unit, whereas the "exhaust" valve 28 remains open for the next step.

After the converted sample has been dried, it undergoes five separate washing steps. During each washing, the sample is washed with dichloroethane-methanol, a well-known wash solvent. Other suitable wash solvents can, however, be easily used. The specific mechanics of delivering the wash solvent from the solvent bottle 34 to the reaction cell 8 is similar to the above-described mechanics of delivering the conversion reagent. Basically, the wash solvent in the solvent bottle 34 is under nitrogen gas pressure due to the opened pressurized solvent valve 35 which delivers nitrogen gas at 4.5 psig from the nitrogen manifold 26. The wash solvent is delivered to the reaction cell 8 under $N_2$ pressure after the solvent valve 36 is opened by the control unit 5. As with the delivery of the reagent, the delivery of the wash solvent is stopped when the pre-programmed control unit causes the solvent valve 36 to close.

During each of the five washings with dichloroethane-methanol, nitrogen gas is bubbled through the mixture in the cell 8. This is accomplished by keeping the "$N_2$ bubble" valve 22 and "exhaust" valve 28 open. The purpose of this bubbling is to effect gentle mixing of the converted, dried sample with the wash solvent. Furthermore, since the heater is on during the entire process, and at the temperature of 65° the solvent rapidly evaporates, the previously discussed reflux action again occurs, thereby thoroughly washing all the tubes and walls in the cell. This refluxing feature results in very efficient washing whereby complete transfer of the sample can be done with as few as five washing cycles. This not only saves time but also solvent, and provides a more concentrated sample for further processing.

After each of the washing steps, the solvent carrying the sample is blown under $N_2$ pressure out of the reaction cell 8 through the anti-backup tube 38, through a T-coupling 24, through the "out" valve 25, and into fraction collector 9. This final step, called the "sample out" step, is performed more specifically as follows. First, the "out" valve 25 is opened by the control unit 5. The "exhaust" valve 28 is then closed. This is the only time during the entire process that the exhaust valve is closed. The "$N_2$ bubble" valve 22 is kept open to prevent the mixture being driven out of the cell 8 into the $N_2$ bubble line 37 at the T coupling 24. The "sample in" valve 21, the "solvent" valve 36, and "reagent" valve 32 remain, of course, in their closed positions. The "$N_2$ flush" valve is then opened by the control unit 5, and the mixture is driven under $N_2$ pressure to the fraction collector 9. At this time the programming means reset to zero, and generates a signal which may be used to inform the main sequencer of readiness to commence a new conversion cycle.

Although the above-described embodiment features the ability to perform all of the desired steps automatically the auto-converter of the present invention includes a manual override capability, whereby any or all of the above-discussed functions can be controlled manually by a function selector switch (not shown) rather than automatically by the programmed control unit.

The control unit 5 is provided with controllable timing means (not shown) for each step whereby the exact duration of each cycle can be regulated. The tube sizes are all standardized, and since the nitrogen gas is employed to pump the reagent and solvent, and the pressure of the nitrogen and liquid viscosities are maintained constant, the quantities of reagent and solvent employed in each cycle may be accurately controlled by the timer. This permits repetitive, exact duplication of process steps and efficient use of materials.

Having thus described the principles of the invention, together with an illustrative embodiment thereof, it is to be understood that, although specific terms are employed, they are used in a generic and descriptive sense and not for purposes of limitation, the scope of the invention being set forth in the following claims.

We claim:

1. Apparatus for the conversion of a sample of a relatively unstable ATZ derivative generated in the Edman sequence analysis of peptides and proteins to a relatively stable derivative comprising:
    (a) a reaction vessel having a lower and an upper part;
    (b) means for maintaining a source of gas under pressure;
    (c) means for receiving said sample to be converted and introducing same into said vessel;
    (d) means for bubbling said gas through said sample in said vessel and simultaneously passing said gas over said sample to dry same;
    (e) means for introducing into said vessel a reagent for conversion of said sample;
    (f) means for regulating the respective temperatures of the upper and lower parts of said vessel to establish reflux conditions therein with respect to said reagent;
    (g) means for separating and removing said reagent from said sample comprising means for bubbling gas therethrough and for simultaneously passing gas over said sample to dry same;
    (h) means for introducing a wash solvent into said vessel;
    (i) means for regulating the respective temperatures of the upper and lower parts of said vessel to establish reflux conditions therein with respect to said wash solvent; and
    (j) means for removing said sample and wash solvent together from said vessel.

2. The apparatus defined in claim 1 further characterized by:
    (k) presettable, timing and control means for controlling the sequence, operation, and duration of operation of each of means (c) through (j).

3. The apparatus defined in claim 1 further characterized by:
    (l) means for applying the pressurized gas of means (b) to each of means (c) through (j) to provide the pumping force for each.

4. A process for the auto conversion of a sample of a relatively unstable ATZ derivative generated in the Edman sequence analysis of peptides and proteins into a relatively stable derivative consisting in the following steps:
    (a) isolating a sample of said derivative in a solvent in a reaction vessel having an upper and a lower part;
    (b) removing said solvent by evaporation;
    (c) introducing a conversion reagent into said vessel;
    (d) mixing said reagent and said sample;
    (e) regulating the respective temperatures of the upper and lower parts of said vessel to establish reflux conditions in said vessel during said conversion;
    (f) permitting the mixed sample and reagent to stand while said reflux conditions of step (e) continue whereby traces of said sample on the upper walls of said vessel during steps (a), (b) and (d) are washed down to the lower portion of said vessel;
    (g) holding said sample and reagent in the mixed state until said conversion reaction is complete;
    (h) removing said reagent from said sample by evaporation;
    (i) introducing a wash solvent into said vessel and bubbling a gas therethrough to mix said sample and said solvent, while regulating the respective temperatures of the lower and upper parts of said vessel to establish reflux conditions with respect to said solvent in said vessel; and (j) removing said sample from said vessel.

5. The process of claim 4 further characterized by;

(k) removing traces of said sample remaining in said vessel after step (j), by repeating steps (i) and (j) until all measurable traces of said sample have been so removed.

6. The process of claim 4 further characterized by accompanying steps (b) and (h) with gentle bubbling of gas through said sample while blowing said gas over same.

7. The process of claim 4 further characterized by carrying out step (d) while bubbling gas through said sample.

8. The process of claim 4 further characterized by both the reagent and the wash solvent having substantially similar boiling points.

9. The process of claim 4 further characterized by said gas being an inert gas.

10. The process of claim 4 further characterized by said reagent including anhydrous methanolic hydrogen chloride and said wash solvent having a boiling point close enough to that of said reagent that the reflux conditions of steps (e) and (i) can proceed without requiring change in the temperature of said vessel.

11. The process of claim 10 further characterized by maintaining the temperature of said vessel at approximately but slightly below the boiling point of said reagent and employing a wash-solvent having a boiling point at least as high as that of said reagent.

12. The process of claim 4 further characterized by employing methanolic hydrogen chloride for the reagent, dichloroethane/methanol (7:3) for the solvent, and heating the lower part of said vessel to about 65° C.

* * * * *